United States Patent [19]

Drake

[11] 4,450,303

[45] May 22, 1984

[54] PROCESS FOR THE OXIDATION OF SECONDARY-ALKYL SUBSTITUTED BENZENES

[75] Inventor: Charles A. Drake, Bartlesville, Okla.

[73] Assignee: Phillips Petroleum Company, Bartlesville, Okla.

[21] Appl. No.: 468,823

[22] Filed: Feb. 23, 1983

[51] Int. Cl.³ .............................................. C07C 179/02
[52] U.S. Cl. ..................................... 568/574; 568/573; 568/569
[58] Field of Search ..................... 568/573, 574, 569

[56] References Cited

U.S. PATENT DOCUMENTS 2,655,545 10/1953 Brüning et al. ...................... 568/573
3,592,857 7/1971 Shinohara ............................ 568/573
4,282,383 8/1981 Dai et al. ............................. 568/574

*Primary Examiner*—Werren B. Lone

[57] ABSTRACT

High selectivities (>90%) for the production of secondary-alkyl substituted benzene hydroperoxides are achieved by heating a secondary-alkyl substituted benzene in the presence of oxygen and a samarium salt. Preferably, a free radical initiator is also present.

11 Claims, No Drawings

PROCESS FOR THE OXIDATION OF SECONDARY-ALKYL SUBSTITUTED BENZENES

This invention relates to an improved process for the oxidation of secondary-alkyl substituted benzenes to form secondary-alkyl substituted benzene hydroperoxides.

The oxidation of alkylated benzenes to alkylated benzene hydroperoxides is known in the art. For example, U.S. Pat. No. 2,655,545 discloses the use of transition metals to oxidize isopropylbenzene to $\alpha,\alpha$-dimethylbenzylhydroperoxide with cerium mentioned as being especially useful.

U.S. Pat. No. 4,282,383 discloses the oxidation of cyclohexylbenzene and dicyclohexylbenzenes to the corresponding hydroperoxides in the presence of t-butyl, cumene, or p-diisopropylbenzene hydroperoxides and a free radical initiator.

While the above systems and others known in the art are operable, very high selectivity to the desired product is not always obtained. Achieving a high selectivity of the desired product is important because the formation of undesirable by-products is thereby minimized.

When the formation of such by-products is minimized, separation of the desired product from the reaction mixture is more readily achieved. Furthermore, easier recycle of unreacted starting material is also accomplished. Therefore, a process which affords excellent selectivity to the desired product is highly desired.

It is therefore an object of this invention to provide an improved process offering unusually high selectivity for the production of hydroperoxides from alkyl substituted benzenes.

Other aspects, objects, and advantages of the present invention are apparent from the specification and the claims.

In accordance with the present invention, I have discovered that by heating a secondary-alkyl substituted benzene in the presence of oxygen and a samarium salt there is obtained a process wherein a surprisingly high selectivity to the desired hydroperoxide is achieved.

In one presently preferred embodiment of this invention, a selectivity of at least 90 percent has been demonstrated with the use of samarium acetate in the presence of a free radical initiator.

The secondary-alkyl substituted benzenes suitable for use in the present invention are those represented by the general formula:

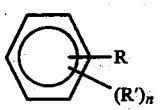
(I)

wherein R is a $C_3$–$C_{20}$ secondary alkyl, cycloalkyl, or secondary alkaryl radical, R' is a $C_1$ to $C_{10}$ alkyl, aryl, or alkaryl radical and n is 0–5. Exemplary compounds falling under formula (I) include cyclohexylbenzene, cumene, sec-butylbenzene, sec-pentylbenzene, p-methyl-sec-butylbenzene, 1,4-diphenylcyclohexane, para-dicyclohexylbenzene, sec-hexylbenzene, and mixtures thereof. Presently preferred is cyclohexylbenzene.

The samarium salt used in the present invention are those samarium salts represented by the formula:

$$R''COOSm \quad (II)$$

wherein R'' is a $C_1$ to $C_{20}$ alkyl, aryl, alkaryl or aralkyl radical. The samarium salts contemplated for use in the present invention include formates, acetates, propionates, butyrates, benzoates, naphthenates, stearates, palmitates, and mixtures thereof. Presently preferred are samarium salts containing 1 to 4 carbon atoms because of their availability and relatively low cost.

In the process of the present invention, the secondary-alkyl substituted benzene compounds of formula (I) are oxidized to their corresponding secondary-alkyl substituted hydroperoxides. Examples of such conversions include cyclohexylbenzene to cyclohexylbenzene hydroperoxide, cumene to cumene hydroperoxide, p-methyl-sec-butylbenzene to p-methyl-sec-butylbenzene hydroperoxide, sec-butylbenzene to sec-butylbenzene hydroperoxide, sec-pentylbenzene to sec-pentylbenzene hydroperoxide, sec-hexylbenzene to sec-hexylbenzene hydroperoxide. The presently preferred conversion is cyclohexylbenzene to cyclohexylbenzene hydroperoxide.

The process of the present invention is carried out conveniently by admixing the secondary-alkyl substituted benzene with the appropriate samarium salt and preferably, a small amount (0.1–10 wt %) of a free radical initiator and maintaining the mixture in the presence of oxygen or a gaseous mixture rich in oxygen such as air at a temperature in the broad range of from about 60°–200° C., with 80°–150° C. preferred.

The free radical initiator employed in the process of the invention can be any of the azo type free radical initiators described in Encyclopedia of Polymer Science and Technology, Vol. 2, page 278 et seq., 1965 or any of the peroxide type free radical initiators described in the same publication at Vol. 9, page 814 et seq., 1968. Illustrative of azo type free radical initiators are 2,2'-azobis(aliphatic nitriles) such as 2,2'-azobisisopropionitrile, 2,2'-azobisisobutyronitrile, 2,2'-azobishexanonitrile, and the like, and azobisalkanes such as 1,1'-azobisbutane, 1,1'-azobishexane, and 1,1'-azobisoctane. Illustrative of peroxide type free radical initiators are alkylaromatic peroxides such as dicumyl peroxide; dialkyl peroxides such as di-t-butyl peroxide, diisobutyl peroxide, diisopropyl peroxide, and diisohexyl peroxide; diperoxy ketals such as 2,2'-bis(t-butyl-peroxy)butane and n-butyl 4,4'-bis(t-butylperoxy)valerate; diacyl peroxides such as dibenzoyl peroxide, diacetyl peroxide, dilauroyl peroxide, and dipropionyl peroxide; peroxy esters such as t-butyl peroxypivalate, t-butyl peroxyacetate, and t-butyl peroxybenzoate; dialkyl peroxydicarbonates such as di-isobutyl peroxydicarbonate, and dihexyl peroxydicarbonate; ketone peroxides such as methyl ethyl ketone peroxide, and cyclohexanone peroxide; and hydroperoxides such as cumene hydroperoxide and t-butyl hydroperoxide.

The amount of free radical initiator employed in the process of the invention is catalytic and advantageously is within the range of about 0.1 percent to about 5 percent by weight based on the amount of starting material. Preferably, the amount of free radical initiator employed in the reaction is within the range of about 0.5 percent to about 1.0 percent by weight.

The amount of samarium salt employed in the present invention is in the range of about 0.05 to about 5 weight percent based on the weight of the secondary-alkyl substituted benzene used as starting material. Preferably, the amount employed is from about 0.1 to 2 weight percent.

Generally, the reaction time for batch reaction will be from about 1 hour to about 10 hours, preferably about 2 to 8 hours. For continuous runs, contact times of 5 minutes to 5 hours, preferably 30 minutes to 3 hours can be employed.

While the pressure at which the process of the present invention is carried out is not thought to be critical, it is broadly from about atmospheric to 1000 psig with about 50–300 psig preferred.

The reaction conditions are maintained in the desired range until the end point of the reaction is reached. The end point is the point at which the initially fast rate of formation of hydroperoxide begins to subside. The end point is readily determinable by routine analytical procedures, such as high pressure liquid chromatography (HPLC), infrared or nuclear magnetic resonance spectroscopy carried out on an aliquot of the reaction mixture.

The reaction product may then be isolated by conventional procedures such as distillation, advantageously under reduced pressure. The residual product can, if desired, be purified by conventional procedures such as column chromatography or fractional recrystallization.

As set forth above, the use of samarium salts in accordance with the present invention enables the oxidation of a secondary-alkyl substituted benzenes, such as cyclohexylbenzene, to be accomplished with high selectivity to the corresponding hydroperoxide such as cyclohexylbenzene hydroperoxide. As will be seen from the data set forth in the Example below, the use of samarium acetate results in product selectivity higher than 90 percent.

The secondary-alkyl substituted benzene hydroperoxides produced in accordance with the present invention are useful as intermediates in the formation of phenols and ketones.

The following example further illustrates the present invention.

EXAMPLE

A series of runs were carried out in a 300 mL stainless steel Autoclave Engineers Magnedrive stirred tank reactor. The following reagents were charged to the reactor: 49 g of cyclohexylbenzene (CHB), 1 g of cumene hydroperoxide, and 0.1 g (0.2 wt %) of lanthanide metal acetate to be tested for promoting activity. The reactor was then sealed, pressurized to 180 psig with $O_2$, and heated to about 120° C. for four hours.

Results are presented in the following Table:

TABLE

| Run No. | Additive | Reaction Temp. °C. | Maximum Pressure, psig | CHB Conversion | Selectivity to CHBHP |
|---|---|---|---|---|---|
| 1 | None | 120 | 193 | 17.4 | 74.2 |
| 2 | Cerium acetate | 118 | 193 | 23.3 | 62.7 |
| 3 | Samarium acetate | 119 | 222 | 12.3 | 90.7 |
| 4 | Lanthanum acetate | 120 | 210 | 23.6 | 53.4 |
| 5 | Yttrium acetate | 120 | 207 | 14.4 | 81.8 |
| 6 | Erbium acetate | 118 | 210 | 19.2 | 73.2 |

Conversion and selectivity data for Runs 1–6 were obtained by gas chromatography analysis with internal standard.

The above data demonstrate that the use of samarium acetate in the reaction mixture (Run 3) significantly improves the selectivity to CHB compared to the selectivities achieved when no additive was used (Run 1) or when some other lanthanide salt was employed (Runs 2, 4, 5, and 6).

Reasonable variations and modifications are possible from the foregoing without departing from the scope and spirit of the present invention.

I claim:

1. A process for the production of a secondary alkyl substituted benzene hydroperoxide comprising heating a secondary alkyl substituted benzene of the formula

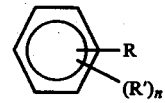

wherein R is a $C_3$ to $C_{20}$ secondary alkyl, cycloalkyl, or secondary alkaryl radical, R' is a $C_1$ to $C_{10}$ alkyl, aryl or alkaryl radical, and n is 0 to 5, in the presence of oxygen and from about 0.05 to 5 weight percent based on the weight of said said secondary-alkyl substituted benzene, of a samarium salt of the formula R"COOSm wherein R" is a $C_1$ to $C_{20}$ alkyl, aryl, alkaryl, or aralkyl radical, at a temperature of about 60° C. to 200° C.

2. A process according to claim 1 wherein said secondary-alkyl substituted benzene is cyclohexylbenzene.

3. A process according to claim 1 wherein said samarium salt is present in an amount from about 0.1 to 2 weight percent.

4. A process according to claim 1 wherein said samarium salt is samarium acetate.

5. A process according to claim 1 wherein said temperature is from about 80° C. to about 150° C.

6. A process according to claim 1 wherein the reaction time is from about 1 hour to about 10 hours.

7. A process according to claim 6 wherein said reaction time is from about 2 hours to about 8 hours.

8. A process according to claim 7 carried out at a pressure from about atmospheric to 1000 psig.

9. A process according to claim 8 wherein said pressure is from about 50 to about 300 psig.

10. A process according to claim 1 carried out in the presence of a free radical initiator selected from the group consisting of azo-type compounds and peroxide compounds.

11. A process according to claim 10 wherein said free radical initiator is cumene hydroperoxide, said samarium salt is samarium acetate, and said secondary-alkyl substituted benzene is cyclohexylbenzene.

* * * * *